United States Patent
Kulkarni et al.

(10) Patent No.: US 9,259,383 B2
(45) Date of Patent: Feb. 16, 2016

(54) COLOURING PRE-MIX FOR USE IN COLOURING OF A COSMETIC COMPOSITION

(71) Applicant: Coty Inc., New York, NY (US)

(72) Inventors: Rupali A. Kulkarni, Bridgewater, NJ (US); Ralph Macchio, Sparta, NJ (US); Leslie C. Smith, Crassier (CH)

(73) Assignee: COTY INC., New York, NY (US)

( * ) Notice: Subject to any disclaimer, the term of this patent is extended or adjusted under 35 U.S.C. 154(b) by 521 days.

(21) Appl. No.: 13/779,108

(22) Filed: Feb. 27, 2013

(65) Prior Publication Data

US 2013/0224132 A1    Aug. 29, 2013

Related U.S. Application Data

(60) Provisional application No. 61/604,701, filed on Feb. 29, 2012.

(30) Foreign Application Priority Data

Feb. 29, 2012 (EP) .................................. 12157557

(51) Int. Cl.

| | |
|---|---|
| *A61K 8/97* | (2006.01) |
| *A61K 8/34* | (2006.01) |
| *A61K 8/37* | (2006.01) |
| *A61K 8/39* | (2006.01) |
| *A61Q 1/02* | (2006.01) |
| *A61Q 1/04* | (2006.01) |
| *A61Q 5/02* | (2006.01) |
| *A61Q 5/12* | (2006.01) |
| *A61Q 1/10* | (2006.01) |
| *A61Q 13/00* | (2006.01) |
| *A61Q 15/00* | (2006.01) |
| *A61Q 17/04* | (2006.01) |
| *A61Q 19/00* | (2006.01) |
| *A61Q 19/10* | (2006.01) |

(52) U.S. Cl.
CPC . *A61K 8/97* (2013.01); *A61K 8/345* (2013.01); *A61K 8/37* (2013.01); *A61K 8/39* (2013.01); *A61Q 1/02* (2013.01); *A61Q 1/04* (2013.01); *A61Q 1/10* (2013.01); *A61Q 5/02* (2013.01); *A61Q 5/12* (2013.01); *A61Q 13/00* (2013.01); *A61Q 15/00* (2013.01); *A61Q 17/04* (2013.01); *A61Q 19/00* (2013.01); *A61Q 19/004* (2013.01); *A61Q 19/10* (2013.01); *A61K 2800/43* (2013.01)

(58) Field of Classification Search
None
See application file for complete search history.

(56) References Cited

U.S. PATENT DOCUMENTS

| | | |
|---|---|---|
| 5,968,535 A | 10/1999 | Mansfeld |
| 2003/0068295 A1 | 4/2003 | Rohde |
| 2003/0161897 A1 | 8/2003 | Shanbrom |

FOREIGN PATENT DOCUMENTS

| | | |
|---|---|---|
| CN | 100408018 | 9/2006 |
| JP | 2006325902 | 12/2006 |
| WO | 90/01270 A1 | 2/1990 |

OTHER PUBLICATIONS

European Search Report and Opinion dated Jul. 16, 2012 for European Patent Application No. 12157557, filed Feb. 29, 2012, consisting of 4 pages.

*Primary Examiner* — Bethany Barham
*Assistant Examiner* — Barbara Frazier
(74) *Attorney, Agent, or Firm* — Novak Druce Connolly Bove + Quigg LLP

(57) ABSTRACT

The present invention provides a colouring pre-mix for use in colouring of a cosmetic composition and a coloured cosmetic composition including the same, wherein the colouring pre-mix includes 45-80 wt-% benzyl benzoate; 20-49 wt-% dipropylene glycol; 0.00001-5 wt-% colouring plant extracts; and optionally 0.00001-5 wt-% colorants; with the provision that the content of benzyl benzoate exceeds the content of dipropylene glycol, wherein all data given in wt-% refer to the total weight of the colouring pre-mix.

16 Claims, No Drawings

COLOURING PRE-MIX FOR USE IN COLOURING OF A COSMETIC COMPOSITION

CROSS-REFERENCE TO RELATED APPLICATIONS

This application claims the benefit of U.S. Provisional Application Ser. No. 61/604,701, filed Feb. 29, 2012 and European Patent Application No. 12157557.5, filed Feb. 29, 2012, which are hereby incorporated by reference in their entirety, for all purposes, herein.

FIELD OF THE INVENTION

The present invention refers to a colouring pre-mix which, in particular, is stable and can be used to impart colour to a cosmetic composition.

BACKGROUND

It is known to impart colour to a cosmetic composition by addition of colorants or pre-formulated colouring compositions. Among the colorants used to impart colour to a cosmetic composition colorants derived from natural resources like e.g. colouring plant extracts attain more and more attention. However, in order to ensure widespread utility of pre-formulated colouring compositions, pre-formulated colouring compositions are needed that exhibit suitable stability and lead to coloured cosmetic compositions which are washable from fabrics.

SUMMARY

An object of the present invention is to provide a colouring pre-mix comprising colouring plant extract, wherein the pre-mix is stable and can be used to impart colour to a cosmetic composition.

It is another object of the present invention to provide a coloured cosmetic composition, wherein the cosmetic composition comprises the colouring pre-mix of the invention and wherein washability of the cosmetic composition of fabrics is improved.

DETAILED DESCRIPTION

According to the invention a colouring pre-mix is provided which is suitable for use in colouring a cosmetic composition, wherein the colouring pre-mix of the invention comprises or consists of:

| | |
|---|---|
| 45-80 wt-% | benzyl benzoate; |
| 20-49 wt-% | dipropylene glycol; |
| 0.00001-5 wt-% | colouring plant extracts; and optionally |
| 0.00001-5 wt-% | further colorants; | with the provision that the content of benzyl benzoate exceeds the content of dipropylene glycol, wherein all data given in wt-% refer to the total weight of the colouring pre-mix.

It has surprisingly been found that the colouring pre-mix of the invention is considerably stable when used in a cosmetic composition. Even after 8 weeks at 45° C., no precipitate has been found. The colouring pre-mix has successfully completed three cycles of freeze/thaw conditions and can successfully be stored at 40° C. or even 50° C. without noticeable degeneration.

The colouring pre-mix of the invention comprises as solvent a mixture of benzyl benzoate and dipropylene glycol, wherein the content of benzyl benzoate in the final colouring pre-mix of the invention exceeds the content of dipropylene glycol. Thus, the colouring pre-mix always comprises more benzyl benzoate than dipropylene glycol when measured in wt-% referenced to the total weight of the colouring pre-mix.

Preferably, the colouring pre-mix of the invention comprises 45 to 80 wt-% benzyl benzoate, more preferably 45 to 75 wt-%, even more preferably 50 to 75 wt-%, wherein all data given in wt-% refer to the total weight of the colouring pre-mix.

The colouring pre-mix of the invention preferably comprises 20 to 49 wt-% dipropylene glycol, more preferably 25 to 45 wt-%, even more preferably 30 to 45 wt-%, wherein all data given in wt-% refer to the total weight of the colouring pre-mix.

In a particular preferred embodiment the colouring pre-mix comprises 45 to 75 wt-% benzyl benzoate and 25 to 45 wt-% dipropylene glycol, wherein all data given in wt-% refer to the total weight of the colouring pre-mix.

In another particularly preferred embodiment the colouring pre-mix comprises 50 to 75 wt-% benzyl benzoate and 30 to 45 wt-% dipropylene glycol, wherein all data given in wt-% refer to the total weight of the colouring pre-mix.

The colouring pre-mix of the invention comprises one or more colouring plant extracts. A colouring plant extract is an extract of a plant or a part of a plant that is capable of imparting a colour impression when added to a composition. The colouring plant extract may be manufactured by any method of extracting a plant or a part thereof. The skilled person is well aware of suitable techniques to prepare a plant extract. A plant extract may be prepared by pressing, maceration or extruding a plant or a part thereof like e.g. the fruit or root of a plant. Alternatively, a plant extract may be prepared by using a solvent for extraction of a plant or a part thereof. The colouring plant extract may be a juice of a fruit of a plant or a concentrate thereof. Alternatively or in addition, the colouring plant extract may comprise or consist of a water-based, alcohol-based or oil-based extract of a plant or a part thereof. Typically the following parts of a plant are used for preparation of a colouring plant extract: flower, leaf, fruit, stem, stipe and/or root. Preferably the colouring plant extract is fruit juice, fruit juice concentrate, water-based, alcohol-based or oil-based extracts of the flower, leaf, fruit, stem, stipe and/or root. The colouring plant extract may be provided in liquid form, in solid form or in any other form or mixture thereof. Preferably the colouring plant extract is provided in liquid or freeze dried form.

The colouring plant extract can be derived from any plant, provided the plant extract is capable of imparting a colour impression to a cosmetic composition. Preferably a colouring plant extract derived from flowering plants of parts thereof is used in the colouring pre-mix of the invention. Preferably, the colouring plant extract is *Rubus fruticosus* (Blackberry) juice (INCI name) or a concentrate thereof, *Malva sylvestris* flower extract (INCI name) or *Fragaria vesca* leaf extract (INCI name). Particularly preferred, the colouring plant extract is *Rubus fruticosus* (Blackberry) juice (INCI name) or a concentrate thereof The colouring pre-mix comprises 0.00001 to 5 wt-% colouring plant extracts, preferably 0.0005 to 1 wt-%, more preferably 0.0005 to 0.8 wt-%, wherein all data given in wt-% refers to the total weight of the colouring pre-mix of the invention. The whole content of colouring plant extracts of the colouring pre-mix of the invention can be prepared of one single plant extract or of a mixture of two or more different plant extracts. The colouring plant extracts of the colouring pre-mix of the invention preferably comprise or consist of cosmetically acceptable plant extracts. A colouring plant extract is regarded as cosmetically acceptable if, when used in a concentration of up to 0.1 wt-% in a cosmetic composition, is non-irritating to human skin. The skilled person is well aware of methods how to test if a given plant extract is cosmetically acceptable or not without undue burden.

In order to further improve or modify the colouring effect of the colouring pre-mix, the colouring pre-mix of the invention optionally may comprise 0.00001-5 wt-% further colorants, preferably 0.01 to 2 wt-%, wherein all data given in wt-% refers to the total weight of the colouring pre-mix of the invention. Said further colorants comprise or consist of one or more colorants that are not colouring plant extracts in the sense of the present invention. Basically any colorant capable of imparting a colour impression to a cosmetic composition can be used as further colorant. Preferably, the further colorant is a cosmetically acceptable colorant. Examples of suitable colorants that can be used as further colorants are Green 6 (EU-CL61565, Japan-Midori202), Yellow 5 (EU-CL19140, Japan-Ki4), Violet 2 (EU-CL6075, Japan-Murasaki201), Red 17 (EU-CL26100, Japan-Aka225), Blue 1 (EU-CL42090, Japan-Ao1), Red 27 (EU-CL45410, Japan-Aka218), Green 5, Orange 4, Red 33, Yellow 10, Green 3, Red 4, Yellow 5, Yellow 6 and/or any mixture thereof. Preferably colorants are used selected from Green 6 (EU-CL61565, Japan-Midori202), Yellow 5 (EU-CL19140, Japan-Ki4), Violet 2 (EU-CL6075, Japan-Murasaki201), Red 17 (EU-CL26100, Japan-Aka225), Blue 1 (EU-CL42090, Japan-Ao1), Red 27 (EU-CL45410, Japan-Aka218) and/or any mixture thereof.

In a preferred embodiment, the colouring pre-mix of the invention comprises or consists of:

| | |
|---|---|
| 55.2 to 60.2 wt-% | benzyl benzoate; |
| 39.7 to 44.7 wt-% | dipropylene glycol; |
| 0.05 to 0.2 wt-% | Green 6 (EU-CL61565, Japan-Midori202); |
| 0.05 to 0.2 wt-% | Yellow 5 (EU-CL19140, Japan-Ki4); |
| 0.05 to 0.1 wt-% | Violet 2 (EU-CL6075, Japan-Murasaki201); |
| 0.01 to 0.05 wt-% | Red 17 (EU-CL26100, Japan-Aka225); |
| 0.0005 to 0.002 wt-% | *rubus fruticosus* (blackberry) juice. |

In another preferred embodiment, the colouring pre-mix of the invention comprises or consists of:

| | |
|---|---|
| 58.2 wt-% | benzyl benzoate; |
| 41.4 wt-% | dipropylene glycol; |
| 0.125 wt-% | Green 6 (EU-CL61565, Japan-Midori202); |
| 0.125 wt-% | Yellow 5 (EU-CL19140, Japan-Ki4); |
| 0.075 wt-% | Violet 2 (EU-CL6075, Japan-Murasaki201); |
| 0.03 wt-% | Red 17 (EU-CL26100, Japan-Aka225); |
| 0.0012 wt-% | *rubus fruticosus* (blackberry) juice; and optionally water. |

The present invention is also directed to a coloured cosmetic composition comprising the colouring pre-mix of the invention.

The coloured cosmetic composition of the invention comprises the colouring pre-mix of the invention in a concentration of 0.015 to 15 wt-%, wherein all data given in wt-% refer to the total weight of the coloured cosmetic composition. Preferably, the coloured cosmetic composition comprises 0.15 to 10 wt-% of the colouring pre-mix of the invention, more preferably, the coloured cosmetic composition comprises 0.5 to 5 wt-% of the colouring pre-mix of the present invention. It has been found that, if the colouring pre-mix of the invention is used in a concentration range specified above, the coloured cosmetic composition exhibits a strong, well noticeable colour impression, while the resulting coloured cosmetic composition remains washable of fabrics. If the coloured cosmetic composition comprises 0.5 to 5 wt-% of the colouring pre-mix, the resulting coloured cosmetic composition is strong in colour impression while the coloured cosmetic composition remains washable of fabrics so that no residual staining is noticeable even after one wash cycle.

The coloured cosmetic composition of the invention can be any kind of cosmetic composition; preferably the coloured cosmetic of the present invention is an alcohol-based or alcohol/water mixture-based cosmetic composition.

The coloured cosmetic compositions of the invention can be e.g. emulsions, creams, lotions, sprays, shampoos, shower gels, shower oils, bath products, foam baths, perfumes, fragrances, eau de toilettes (EDT), aftershaves, shaving balms, face lotions, hair conditioners, skin gels, deodorants, sun creams, sun lotions, after-sun products, body bronzers, sun sprays, sun milks, mascaras, foundations, make-up, lipsticks and/or lip balms. Preferably, the coloured composition of the invention is an eau de toilette (EDT).

In another embodiment, the coloured cosmetic composition of the invention is an alcohol-based or alcohol/water mixture-based perfume, eau de toilette (EDT), aftershave or deodorant.

In a particular embodiment, the coloured cosmetic composition consists of:

| | |
|---|---|
| 70 to 75 wt-% | alcohol (ethyl alcohol); |
| 10 to 15 wt-% | fragrance; |
| 8 to 12 wt-% | water; |
| 1.0 to 1.5 wt-% | ethylhexyl methoxycinnamate; |
| 0.65 to 1.2 wt-% | benzyl benzoate; |
| 0.5 to 1.0 wt-% | butylphenyl methylpropional; |
| 0.4 to 0.8 wt-% | dipropylene glycol; |
| 0.15 to 0.5 wt-% | benzyl salicylate; |
| 0.15 to 0.5 wt-% | ethylhexyl salicylate; |
| 0.15 to 0.5 wt-% | benzophenone-3; |
| 0.2 to 0.4 wt-% | limonene; |
| 0.1 to 0.3 wt-% | butyl methoxydibenzoylmethane; |
| 0.1 to 0.2 wt-% | hydroxycitronellal; |
| 0.08 to 0.12 wt-% | alpha-isomethyl ionone; |
| 0.07 to 0.1 wt-% | hydroxyisohexyl 3-cyclohexene carboxaldehyde; |
| 0.07 to 0.1 wt-% | citronellol; |
| 0.05 to 0.1 wt-% | t-butyl alcohol; |
| 0.05 to 0.07 wt-% | geraniol; |
| 0.02 to 0.05 wt-% | linalool; |
| 0.02 to 0.05 wt-% | acrylates/octylacrylamide copolymer; |
| 0.02 to 0.05 wt-% | coumarin; |
| 0.01 to 0.02 wt-% | BHT; |
| 0.002 to 0.05 wt-% | hydrolyzed jojoba esters; |
| 0.002 to 0.003 wt-% | citral; |
| 0.0015 to 0.002 wt-% | Green 6 (EU-CL61565, Japan-Midori202); |
| 0.0015 to 0.002 wt-% | Yellow 5 (EU-CL19140, Japan-Ki4); |
| 0.001 to 0.0015 wt-% | Violet 2 (EU-CL6075, Japan-Murasaki201); |
| 0.0004 to 0.0005 wt-% | Red 17 (EU-CL26100, Japan-Aka225); and |
| 0.000015 to 0.00002 wt-% | *rubus fruticosus* (blackberry) juice. |

The present invention is also directed to a method of imparting colour to a cosmetic composition. The method of the invention is characterized by the step of adding a colouring pre-mix of the present invention. If the colouring pre-mix of the invention is added to a final concentration of 0.015 to 15 wt-%, preferably of 0.15 to 10 wt-%, more preferably of 0.5 to 5 wt-%, wherein all data given in wt-% refer to the total weight of the coloured cosmetic composition, the resulting coloured cosmetic composition exhibits a strong colour impression but remains washable from fabrics.

The invention will hereinafter be explained in more detail by means of examples.

EXAMPLES

Example 1

Colouring Pre-mix of the Invention Based on *Rubus Fruticosus* (Blackberry) Juice

TABLE 1

| COMMON NAME | INCI NAME | CAS # | Ranges wt-% |
|---|---|---|---|
| Benzyl benzoate | Benzyl benzoate | 120-51-4 | 55.7-60.7 |
| Dipropylene glycol | Dipropylene glycol | 110-98-5 | 39.7-44.7 |
| Green 6 | Green 6 (EU-CL61565, Japan-Midori202) | 128-80-3 | 0.05-0.2 |
| Yellow 5 | Yellow 5 (EU-CL19140, Japan-Ki4) | 1934-21-0 | 0.05-0.2 |
| Violet 2 | Violet 2 (EU-CL6075, Japan-Murasaki201) | 81-48-1 | 0.05-0.1 |
| Red 17 | Red 17 (EU-CL26100, Japan-Aka225) | 85-86-9 | 0.01-0.05 |
| Blackberry juice concentrate | *rubus fruticosus* (blackberry) juice | n/a | 0.0005-0.002 |
| water | water | | ad 100 |

*Rubus fruticosus* (blackberry) juice is produced from a mechanical maceration of the fruit and then further concentrated by heat to remove excess water. No extraction solvents are used. No preservatives are used.

Colouring pre-mix's prepared according to Table 1 exhibited neither any precipitation nor any noticeable physical change even after storage at 45° C. for 8 weeks.

Example 2

Colouring Pre-mix of the Invention Based on *Rubus Fruticosus* (Blackberry) Juice

TABLE 2

| COMMON NAME | INCI NAME | CAS # | Ranges wt-% |
|---|---|---|---|
| Benzyl benzoate | Benzyl benzoate | 120-51-4 | 56.72-58.72 |
| Dipropylene glycol | Dipropylene glycol | 110-98-5 | 40.86-42.86 |
| Green 6 | Green 6 (EU-CL61565, Japan-Midori202) | 128-80-3 | 0.05-0.2 |
| Yellow 5 | Yellow 5 (EU-CL19140, Japan-Ki4) | 1934-21-0 | 0.05-0.2 |
| Violet 2 | Violet 2 (EU-CL6075, Japan-Murasaki201) | 81-48-1 | 0.05-0.1 |
| Red 17 | Red 17 (EU-CL26100, Japan-Aka225) | 85-86-9 | 0.01-0.05 |
| Blackberry juice concentrate | *rubus fruticosus* (blackberry) juice | n/a | 0.0005-0.002 |
| water | water | | ad 100 |

*Rubus fruticosus* (blackberry) juice is produced from a mechanical maceration of the fruit and then further concentrated by heat to remove excess water. No extraction solvents are used. No preservatives are used.

Colouring pre-mix's prepared according to Table 2 exhibited neither any precipitation nor any noticeable physical change even after storage at 45° C. for 8 weeks.

Example 3

Comparative Colouring Pre-mix Based on Alcohol as Solvent and *Rubus Fruticosus* (Blackberry) Juice

TABLE 3

| COMMON NAME | INCI NAME | CAS # | Ranges wt-% |
|---|---|---|---|
| Ethyl alcohol | alcohol | 64-17-5 | 90-95 |
| Green 6 | Green 6 (EU-CL61565, Japan-Midori202) | 128-80-3 | 0.05-0.2 |
| Yellow 5 | Yellow 5 (EU-CL19140, Japan-Ki4) | 1934-21-0 | 0.05-0.2 |
| Violet 2 | Violet 2 (EU-CL6075, Japan-Murasaki201) | 81-48-1 | 0.05-0.1 |
| Red 17 | Red 17 (EU-CL26100, Japan-Aka225) | 85-86-9 | 0.01-0.05 |
| Blackberry juice concentrate | *rubus fruticosus* (blackberry) juice | n/a | 0.0005-0.002 |
| water | water | | ad 100 |

*Rubus fruticosus* (blackberry) juice is produced from a mechanical maceration of the fruit and then further concentrated by heat to remove excess water. No extraction solvents are used. No preservatives are used.

Colouring pre-mix's prepared according to Table 3 exhibited an intolerable precipitation problem and the resulting pre-mix was not stable.

Example 4

Colouring Pre-mix of the Invention Based on *Fragaria Vesca* Leaf Extract

TABLE 4

| COMMON NAME | INCI NAME | CAS # | Ranges wt-% |
|---|---|---|---|
| Benzyl benzoate | Benzyl benzoate | 120-51-4 | 91.65-93.65 |
| Dipropylene glycol | Dipropylene glycol | 110-98-5 | 5.99-7.99 |
| Green 6 | Green 6 (EU-CL61565, Japan-Midori202) | 128-80-3 | 0.0138-0.0158 |
| Apricot Kernel Oil | *Prunus armeniaca* (Apricot) kernel oil | 72869-69-3 | 0.089-0.109 |
| Violet 2 | Violet 2 (EU-CL6075, Japan-Murasaki201) | 81-48-1 | 0.00871-0.0107 |
| Red 17 | Red 17 (EU-CL26100, Japan-Aka225) | 85-86-9 | 0.21-0.23 |
| Blue 1 | Blue 1 (EU-CL42090, Japan-Ao1) | 3844-45-9 | 0.004-0.006 |
| Red 27 | Red 27 (EU-CL45410, Japan-Aka218) | 13473-26-2 | 0.001-0.003 |
| Strawberry leaves | *fragaria vesca* leaf extract | n/a | 0.0005-0.0015 |
| water | water | | ad 100 |

Colouring pre-mix's prepared according to Table 4 exhibited no precipitation but noticeable physical changes after storage at 45° C. for 8 weeks. Thus, this pre-mix is not regarded as sufficiently stable.

Example 5

Colouring Pre-mix of the Invention Based on *Fragaria Vesca* Leaf Extract

TABLE 5

| COMMON NAME | INCI NAME | CAS # | Ranges wt-% |
| --- | --- | --- | --- |
| Benzyl benzoate | Benzyl benzoate | 120-51-4 | 50.8-52.8 |
| Dipropylene glycol | Dipropylene glycol | 110-98-5 | 46.8-48.8 |
| Green 6 | Green 6 (EU-CL61565, Japan-Midori202) | 128-80-3 | 0.0138-0.0158 |
| Apricot Kernel Oil | *Prunus armeniaca* (Apricot) kernel oil | 72869-69-3 | 0.089-0.109 |
| Violet 2 | Violet 2 (EU-CL6075, Japan-Murasaki201) | 81-48-1 | 0.00871-0.0107 |
| Red 17 | Red 17 (EU-CL26100, Japan-Aka225) | 85-86-9 | 0.21-0.23 |
| Blue 1 | Blue 1 (EU-CL42090, Japan-Ao1) | 3844-45-9 | 0.004-0.006 |
| Red 27 | Red 27 (EU-CL45410, Japan-Aka218) | 13473-26-2 | 0.001-0.003 |
| Strawberry leaves | *fragaria vesca* leaf extract | n/a | 0.0005-0.0015 |
| water | water |  | ad 100 |

Colouring pre-mix's prepared according to Table 5 exhibited neither any precipitation nor any noticeable physical change even after storage at 45° C. for 8 weeks.

Example 6

Colouring Pre-mix of the Invention Based on *Malva Sylvestris* (Mallow) Flower Extract

TABLE 6

| COMMON NAME | INCI NAME | CAS # | Ranges wt-% |
| --- | --- | --- | --- |
| Benzyl benzoate | Benzyl benzoate | 120-51-4 | 69.54-71.54 |
| Dipropylene glycol | Dipropylene glycol | 110-98-5 | 27.72-29.72 |
| Green 6 | Green 6 (EU-CL61565, Japan-Midori202) | 128-80-3 | 0.0016-0.0036 |
| Violet 2 | Violet 2 (EU-CL6075, Japan-Murasaki201) | 81-48-1 | 0.0007-0.0027 |
| Red 17 | Red 17 (EU-CL26100, Japan-Aka225) | 85-86-9 | 0.00069-0.00089 |
| Blue 1 | Blue 1 (EU-CL42090, Japan-Ao1) | 3844-45-9 | 0.018-0.038 |
| Malva blue | *malva sylvestris* (Mallow) flower extract | 84082-57-5 | 0.6-0.8 |
| water | water |  | ad 100 |

Colouring pre-mix's prepared according to Table 6 exhibited neither any precipitation nor any noticeable physical change even after storage at 45° C. for 8 weeks.

Example 7

Colouring Pre-mix of the Invention Based on *Malva Sylvestris* (Mallow) Flower Extract

TABLE 7

| COMMON NAME | INCI NAME | CAS # | Ranges wt-% |
| --- | --- | --- | --- |
| Benzyl benzoate | Benzyl benzoate | 120-51-4 | 66.38-68.38 |
| Dipropylene glycol | Dipropylene glycol | 110-98-5 | 30.91-32.91 |
| Blue 1 | Blue 1 (EU-CL42090, Japan-Ao1) | 3844-45-9 | 0.022-0.042 |
| Melva blue | *malva sylvestris* (Mallow) flower extract | 84082-57-5 | 0.58-0.78 |
| water | water |  | ad 100 |

Colouring pre-mix's prepared according to Table 7 exhibited neither any precipitation nor any noticeable physical change even after storage at 45° C. for 8 weeks.

Example 8

Eau de toilette (EDT) Comprising Colouring Pre-mix of Example 2

TABLE 8

| % w/w | INCI name |
| --- | --- |
| 72.13 | Alcohol (ethyl alcohol) |
| 12.06 | fragrance |
| ad 100 | water |
| 1.2 | ethylhexyl methoxycinnamate |
| 0.87 | benzyl benzoate |
| 0.76 | butylphenyl methylpropional |
| 0.62 | dipropylene glycol |
| 0.32 | benzyl salicylate |
| 0.30 | ethylhexyl salicylate |
| 0.30 | benzophenone-3 |
| 0.28 | limonene |
| 0.20 | butyl methoxydibenzoylmethane |
| 0.16 | hydroxycitronellal |
| 0.10 | alpha-isomethyl ionone |
| 0.09 | hydroxyisohexyl 3-cyclohexene carboxaldehyde |
| 0.08 | citronellol |
| 0.06 | t-butyl alcohol |
| 0.06 | geraniol |
| 0.03 | linalool |
| 0.03 | acrylates/octylacrylamide copolymer |
| 0.03 | coumarin |
| 0.01 | BHT |
| 0.02 | hydrolyzed jojoba esters |
| 0.0024 | citral |
| 0.0019 | Green 6 |
| 0.0019 | Yellow 5 |
| 0.0011 | Violet 2 |
| 0.00045 | Red 17 |
| 0.000019 | *rubus fruticosus* (blackberry) juice |

For preparation of the EDT of Table 8, hydrolyzed jojoba esters and acrylates/octylacrylamide copolymer are preformulated in alcohol and an adequate amount of said preformulation is used for manufacturing of the EDT of Table 8 in order to arrive at the specified concentrations.

EDT prepared according to Table 8 exhibited neither any precipitation nor any noticeable physical change even after storage at 45° C. for 8 weeks. Furthermore, EDT prepared according to Table 8 exhibited only acceptable fade.

Example 9

Textile Testing with EDT of Example 8

Objectives:

This textile test is directed to determine the resistance to staining of a submitted cosmetic composition on cotton, polyester, nylon and acrylic fabric samples after one home laundering cycle (HW for home wash and, if necessary, dry cleaning for recovery).

This textile test is directed to determine the resistance to staining of a submitted cosmetic composition on silk, rayon and wool fabric samples after one dry cleaning cycle in perchloroethylene solvent.

Test Procedure:

The EDT of Example 8 is tested according to Coty's revised Stain Release Test Method. In brief, seven white fabric samples (cotton, polyester, nylon, acrylic, silk, rayon and wool) have been weighed, then four (4) sprays of EDT have been applied to each fabric sample and the fabric samples were weighed again. The weights have been recorded and reported in Table 9. After 15 minutes the stained samples have been evaluated for staining using the AATCC Stain Release Evaluation Procedure where by 5=no staining, 4=slight staining, 3=noticeable staining, 2=severe staining, 1=very severe staining. After 16 to 24 hours the stained fabrics will again be evaluated with the AATCC Stain Release Evaluation Procedure. The cotton, polyester, nylon and acrylic stained fabric samples have been subjected to one (1) home wash cycle (cotton is washed in warm water load; polyester, nylon and acrylic are washed in cold water load); silk, rayon and wool fabric samples have been subjected to one (1) dry cleaning cycle in perchloroethylene solvent. After cleaning the fabric samples have been evaluated for staining using the AATCC Stain Release Evaluation Procedure. If either the cotton, polyester, nylon or acrylic fabric samples are rated at 4.0 or lower, they have been subjected to one (1) recovery cycle in dry cleaning and have been re-evaluated using the AATCC Stain Release Evaluation Procedure. If the stain rating after the cleaning and recovery cycle was 4.0 or greater, the EDT is rated "non-staining", whereas if the stain rating was lower than 4.0, the fabric type is stained and the EDT is rated "may stain >>fabric type<<".

Test results:

TABLE 9

| Care method | Fabric sample | Wt. bef. appl. (g) | Wt. aft. appl. (g) | 15 min | 16-24 hrs | 1x HW rating | 1x DC rating | 1x recov. |
|---|---|---|---|---|---|---|---|---|
| Home wash (HW) | Cotton | 10.7 | 10.9 | 1.0 | 2.0 | 4.0 | n/a | 5.0 |
| | Polyester | 7.7 | 8.0 | 2.0 | 3.0 | 4.0 | n/a | 5.0 |
| | Nylon | 7.4 | 7.7 | 3.0 | 4.5 | 5.0 | n/a | — |
| | Acrylic | 11.5 | 11.8 | 1.0 | 3.0 | 3.5 | n/a | 5.0 |
| Dry cleaning (DC) | Silk | 7.8 | 8.1 | 1.0 | 1.0 | n/a | 4.5 | n/a |
| | Rayon | 13.2 | 13.5 | 1.0 | 3.0 | n/a | 4.5 | n/a |
| | wool | 16 | 16.3 | 1.0 | 2.0 | n/a | 4.5 | n/a |

The weight of the test fabrics was measured in grams (g). The AATCC Stain Release Evaluation Rating System is a numerical rating ranging from 5=no staining, 4=slight staining, 3=noticeable staining, 2=considerable staining, 1=severe staining. After one cycle of home washing if the average stain rating of cotton, polyester, nylon or acrylic is 4.0 or lower, the fabric is subjected to a dry cleaning recovery cycle. Silk, rayon and wool will not be subjected to further care processes after one dry cleaning cycle, regardless of the average stain rating.

Accordingly, the EDT of Example 8 is deemed "non-staining" for nylon after one home wash cycle, is "non-staining" for cotton, polyester and acrylic after one dry cleaning recovery cycle and is also "non-staining" for silk, rayon and wool after a single dry cleaning cycle.

The invention claimed is:

1. A colouring pre-mix for use in colouring of a cosmetic composition, comprising:

| | |
|---|---|
| 45-80 wt-% | benzyl benzoate; |
| 20-49 wt-% | dipropylene glycol; |
| 0.00001-5 wt-% | colouring plant extracts; | with the provision that the content of benzyl benzoate exceeds the content of dipropylene glycol, wherein all data given in wt-% refer to the total weight of the colouring pre-mix and wherein the cumulative weight percent of benzyl benzoate, dipropylene glycol, and colouring plant extracts does not exceed 100 percent.

2. The colouring pre-mix of claim 1, wherein the colouring plant extracts are liquid or freeze dried.

3. The colouring pre-mix of claim 1, wherein the content of benzyl benzoate amounts to 45 to 75 wt-% and the content of dipropylene glycol amounts to 25 to 45 wt-%.

4. The colouring pre-mix of claim 1, wherein the content of benzyl benzoate amounts to 50 to 75 wt-% and the content of dipropylene glycol amounts to 30 to 45 wt-%.

5. The colouring pre-mix of claim 1, wherein the colouring plant extracts comprise one or more cosmetically acceptable plant extracts.

6. The colouring pre-mix of claim 1, wherein the colouring plant extracts are extracts of flowering plants or parts thereof capable of imparting colour to a cosmetic composition.

7. The colouring pre-mix of claim 1, wherein the colouring plant extracts are fruit juice, fruit juice concentrate, water-based, alcohol-based or oil-based extracts of the flower, leaf, fruit, stem, stipe and/or root.

8. The colouring pre-mix of claim 1, wherein the colouring plant extract is *Rubus fruticosus* (Blackberry) juice (INCI name) or a concentrate thereof, *Malva sylvestris* flower extract (INCI name) or *Fragaria vesca* leaf extract (INCI name).

9. The colouring pre-mix of claim 1, further comprising:
   00001-5 wt-% further colorants wherein the further colorants comprise one or more cosmetically acceptable colorants that are not colouring plant extracts.

10. The colouring pre-mix of claim 9, wherein the colorants comprise Green 6 (INCI name), Yellow 5 (INCI name), Violet 2 (INCI name), Red 17 (INCI name), Blue 1 (INCI name), Red 27 (INCI name) or a mixture thereof.

11. The colouring pre-mix of claim 1, comprising:

| | | |
|---|---|---|
| 55.2 to 60.2 | wt-% | benzyl benzoate; |
| 39.7 to 44.7 | wt-% | dipropylene glycol; |
| 0.05 to 0.2 | wt-% | Green 6 (INCI name); |
| 0.05 to 0.2 | wt-% | Yellow 5 (INCI name); |
| 0.05 to 0.1 | wt-% | Violet 2 (INCI name); |
| 0.01 to 0.05 | wt-% | Red 17 (INCI name); |
| 0.0005 to 0.002 | wt-% | *rubus fruticosus* (blackberry) juice. |

12. The colouring pre-mix of claim 11, comprising:

| | | |
|---|---|---|
| 58.2 | wt-% | benzyl benzoate; |
| 41.4 | wt-% | dipropylene glycol; |
| 0.125 | wt-% | Green 6 (INCI name); |
| 0.125 | wt-% | Yellow 5 (INCI name); |
| 0.075 | wt-% | Violet 2 (INCI name); |
| 0.03 | wt-% | Red 17 (INCI name); |
| 0.0012 | wt-% | *rubus fruticosus* (blackberry) juice; and optionally water. |

13. A coloured cosmetic composition comprising 0.015 to 15 wt-% colouring pre-mix of claim 1, wherein the amount of colouring pre-mix given in wt-% refers to the total weight of the cosmetic composition.

14. The coloured cosmetic composition of claim 13, wherein the cosmetic composition is an emulsion, a cream, a lotions, a spray, a shampoo, a shower gel, a shower oil, a bath product, a foam bath, a perfume, a fragrance, an eau de toilette (EDT), an aftershave, a shaving balm, a face lotion, a hair conditioner, a skin gel, a deodorant, a sun cream, a sun lotion, an after-sun product, a body bronzer, a sun spray, a sun milk, a mascara, a foundation, a make-up, a lipstick and/or a lip balm.

15. A coloured cosmetic composition consisting of:

| Wt-%: | | INCI name: |
|---|---|---|
| 70 to 75 | wt-% | alcohol; |
| 10 to 15 | wt-% | fragrance; |
| ad 100 | wt-% | water; |
| 1.0 to 1.5 | wt-% | ethylhexyl methoxycinnamate; |
| 0.65 to 1.2 | wt-% | benzyl benzoate; |
| 0.5 to 1.0 | wt-% | butylphenyl methylpropional; |
| 0.4 to 0.8 | wt-% | dipropylene glycol; |
| 0.15 to 0.5 | wt-% | benzyl salicylate; |
| 0.15 to 0.5 | wt-% | ethylhexyl salicylate; |
| 0.15 to 0.5 | wt-% | benzophenone-3; |
| 0.2 to 0.4 | wt-% | limonene; |
| 0.1 to 0.3 | wt-% | butyl methoxydibenzoylmethane; |
| 0.1 to 0.2 | wt-% | hydroxycitronellal; |
| 0.08 to 0.12 | wt-% | alpha-isomethyl ionone; |
| 0.07 to 0.1 | wt-% | hydroxyisohexyl 3-cyclohexene carboxaldehyde; |
| 0.07 to 0.1 | wt-% | citronellol; |
| 0.05 to 0.1 | wt-% | t-butyl alcohol; |
| 0.05 to 0.07 | wt-% | geraniol; |
| 0.02 to 0.05 | wt-% | linalool; |
| 0.02 to 0.05 | wt-% | acrylates/octylacrylamide copolymer; |
| 0.02 to 0.05 | wt-% | coumarin; |
| 0.01 to 0.02 | wt-% | BHT; |
| 0.002 to 0.05 | wt-% | hydrolyzed jojoba esters; |
| 0.002 to 0.003 | wt-% | citral; |
| 0.0015 to 0.002 | wt-% | Green 6 (EU-CL61565, Japan-Midori202); |
| 0.0015 to 0.002 | wt-% | Yellow 5 (EU-CL19140, Japan-Ki4); |
| 0.001 to 0.0015 | wt-% | Violet 2 (EU-CL6075, Japan-Murasaki201); |
| 0.0004 to 0.0005 | wt-% | Red 17 (EU-CL26100, Japan-Aka225); and |
| 0.000015 to 0.00002 | wt-% | *rubus fruticosus* (blackberry) juice. |

16. A method of imparting colour to a cosmetic composition, the method comprising the step of adding 0.015 to 15 wt-% of a colouring pre-mix of claim 1, wherein the amount of colouring pre-mix given in wt-% refers to the total weight of the final coloured cosmetic composition.

\* \* \* \* \*